(12) United States Patent  (10) Patent No.: US 8,853,194 B2
Chen et al.  (45) Date of Patent: Oct. 7, 2014

(54) STEROL DERIVATIVES AND THEIR SYNTHESIS AND USE

(75) Inventors: Dagang Chen, Yunnan (CN); Haimin Lei, Yunnan (CN)

(73) Assignee: Dagang Chen, Yunnan (CN)

( * ) Notice: Subject to any disclaimer, the term of this patent is extended or adjusted under 35 U.S.C. 154(b) by 212 days.

(21) Appl. No.: 13/387,559

(22) PCT Filed: Jan. 15, 2010

(86) PCT No.: PCT/CN2010/070213
§ 371 (c)(1),
(2), (4) Date: Jan. 27, 2012

(87) PCT Pub. No.: WO2011/011984
PCT Pub. Date: Feb. 3, 2011

(65) Prior Publication Data
US 2012/0130067 A1 May 24, 2012

(30) Foreign Application Priority Data

Jul. 28, 2009 (CN) .......................... 2009 1 0094773

(51) Int. Cl.
*A61K 31/58* (2006.01)
*C07J 71/00* (2006.01)
(52) U.S. Cl.
CPC .................................. *C07J 71/0005* (2013.01)
USPC ........................................... 514/172; 540/62
(58) Field of Classification Search
USPC ........................................... 514/172; 540/62
See application file for complete search history.

(56) References Cited

FOREIGN PATENT DOCUMENTS

| CN | 1358734 A | 7/2002 |
| CN | 101204401 A | 6/2008 |
| CN | 101619089 A | 1/2010 |

OTHER PUBLICATIONS

P. Ramesh, et al., "Synthesis of Melithasterol A, a 5a,6a-Epoxy-7a-hydroxy tl8-Steroid," J. Nat. Prod. 2000, pp. 1420-1421, vol. 63.
Zhang Dong, et al., "Photosensitized oxidation of 7-dehydrocholesterol by Nafion-loaded platinum ( II) terpyridyl acetylide complex, Photographic Science and Photochemistry," Nov. 2003, pp. 405-411, vol. 2I, No. 6.
Fan Gui-Xiang, "Study on synthesis of the 7-dehydrocholesteryl aetate," Chemical Engineering & Equipment, Jul. 2009, pp. 28-35.
Judah Folkman, "What is the Evidence That Tumors are Angiogenesis Dependent?," Journal of National Cancer Institute, 1990, pp. 4-6, vol. 82, No. 1.
Domenico Ribatti, et al., "The Chick Embryo Chorioallantoic Membrane as a Model for in vivo Research on Anti-Angiogenesis," Current Pharmaceutical Biotechnology, 2000, pp. 73-82, vol. 1, No. 1.
TF Greten, et al., "Molecular therapy for the treatment of hepatocellular carcinoma," British Journal of Cancer, 2009, pp. 19-23, vol. 100(1).

*Primary Examiner* — Brenda Coleman
(74) *Attorney, Agent, or Firm* — The Webb Law Firm

(57) ABSTRACT

Sterol derivatives with structural formula I or II are disclosed, wherein R is defined as the description of the invention. Their synthesizing methods and anti-tumor use are also disclosed. Especially, the compound of formula I, in which R is O (i.e. the compound CL 168-6), has the anti-tumor therapeutic index of 49.3. The compound can be used to prepare a medicine for prevention or treatment of immunological diseases and cancers such as liver cancer and lung cancer.

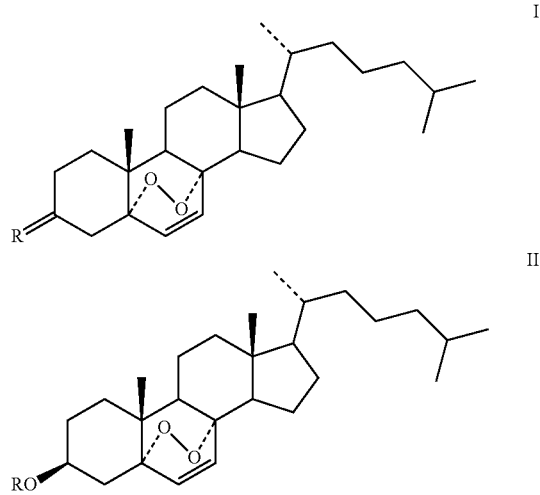

6 Claims, 4 Drawing Sheets

Blank Control Group     Suramin (4ug/embryo)

CL168-6 (2ug/embryo)    CL168-6 (4ug/embryo)    CL168-6 (8ug/embryo)

STEROL DERIVATIVES AND THEIR SYNTHESIS AND USE

FIELD OF THE INVENTION

The present invention relates to pharmaceutical compounds in the field of chemical and biological sciences, particularly to anti-tumor drugs CL168 with general structural formula I and II, and their synthesis method and use.

BACKGROUND OF THE INVENTION

Tumor is one of the main diseases harmful to human healthy, and comes second in mortalities of various diseases. A large number of clinical practices prove that, when killing tumor cells, chemo-treatment and radiation treatment simultaneously have significant damage effect on normal cells. These treatments do serious damage to the hematopoietic system and immune function of human beings, and easily lead to patients' deaths. All of the tumor cells are dependent on vascular, and angiogenesis is an important step in the growth and metastasis of a tumor. For both primary tumors and secondary tumors, angiogenesis occurs once their growth diameter is more than 2 mm, and then the tumors grow fast and the metastasis occurs. (Folkman J. what is the evidence that tumors are angiogenesis department? J Natl Cancer Inst. 1990, 82:4-6.)

At present, drugs for treating tumors could mainly be divided into three types: cytotoxic drugs, radiotherapy and chemotherapy adjunctive drugs, and angiogenesis inhibitors. Currently angiogenesis inhibitors are a type of very promising antitumor drugs.

SUMMARY OF THE INVENTION

The compounds of the present invention, named CL168, are a type of compounds with novel structural skeletons, clear activities and specific anti-tumor targets, selected from structural modifications of hundreds of natural products based on selection basis of CAM model (Ribatti D, Vacca A, et al. The chick embryo chorioallantoic membrane as a model for in vivo research on anti-angiogenesis. Curr Pharm Biotechnol. 2000 July; 1(1):73-82) and VEGF (Gretten T F, Korangy F, et al. Molecular therapy for the treatment of hepatocellular carcinoma. Br J Cancer. 2009 Jan. 13; 100(1):19-23). Pharmacological experiments show that these compounds have significant anti-tumor effects, wherein CL168-6 has an anti-tumor therapeutic index of 49.3, and can be used for preparing drugs for the prevention and treatment of cancers, such as liver cancer, lung cancer, etc., and immunological diseases.

One of the objectives of the present invention is to provide a synthesizing route for preparing CL168 as shown by general formula I and intermediates thereof.

The second objective of the present invention is to provide a synthesizing route for preparing CL168 as shown by general formula II and intermediates thereof.

The third objective of the present invention is to provide applications of CL168 of general formulas I & II and intermediates thereof, on anti-tumor and immune-improving researches.

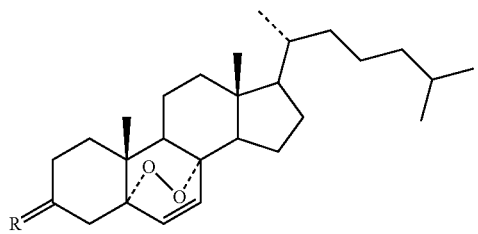

I

It is CL168-6 when R represents O.
R represents S, NH or $SO_2$.

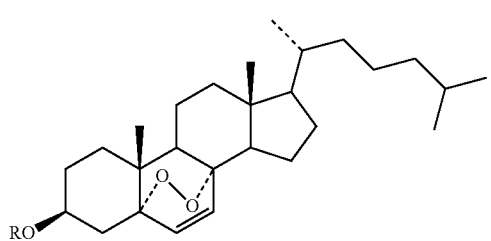

II

R represents a $C_{2-25}$ alkyl group, aryl group, aryl group substituted with electron-donating group or electron withdrawn group, $C_{3-6}$ alkynyl group, alkenyl group, $C_{3-9}$ cycloalkyl group, $C_{3-9}$ stubstituted heterocycloalkyl group, $C_{1-20}$ fatty acyl group, aromatic acyl group, sulfonyl, cinnamoyl, caffeoyl, galloyl, feruloyl, benzoyl, L-aliphatic amino acyl, or L-aromatic amino acyl.

The objectives of the present invention can be realized by the following procedures.

The compound CL168 represented by the general structural formula I can be prepared by a method including the following steps:

(1) dissolving cholesterol (Compound 2) in an organic solvent to produce cholesteryl acetate (Compound 3) by reacting the cholesterol with acetic anhydride under the catalysis of a catalyst, at a certain temperature;

(2) dissolving the Compound 3 in an organic solvent to produce 7-bromocholesten-3-ol acetate (Compound 4) by reacting Compound 3 with a bromide reagent under the catalysis of a catalyst, at a certain temperature;

(3) dissolving the Compound 4 in an organic solvent to produce 7-dehydrocholesten-3-ol acetate (Compound 5) by elimination reaction with a base at a certain temperature;

(4) dissolving the Compound 5 in an organic solvent to produce 7-dehydrocholesterol (Compound 6) by hydrolyzing Compound 5 with a base at a certain temperature;

(5) dissolving the Compound 6 in an organic solvent to produce 5α, 8α-cyclicobioxygen-6-cholesten-3-ol (Compound 7) by oxidizing Compound 6 with an oxidant at a certain temperature;

(6) dissolving the Compound 7 in an organic solvent to produce 5α, 8α-cyclicobioxygen-6-cholesten-3-one (Compound 1, i.e. CL168-6) by oxidizing Compound 7 with an oxidant at a certain temperature;

The reaction equations in the above-mentioned steps (1)-(6) are as follows:

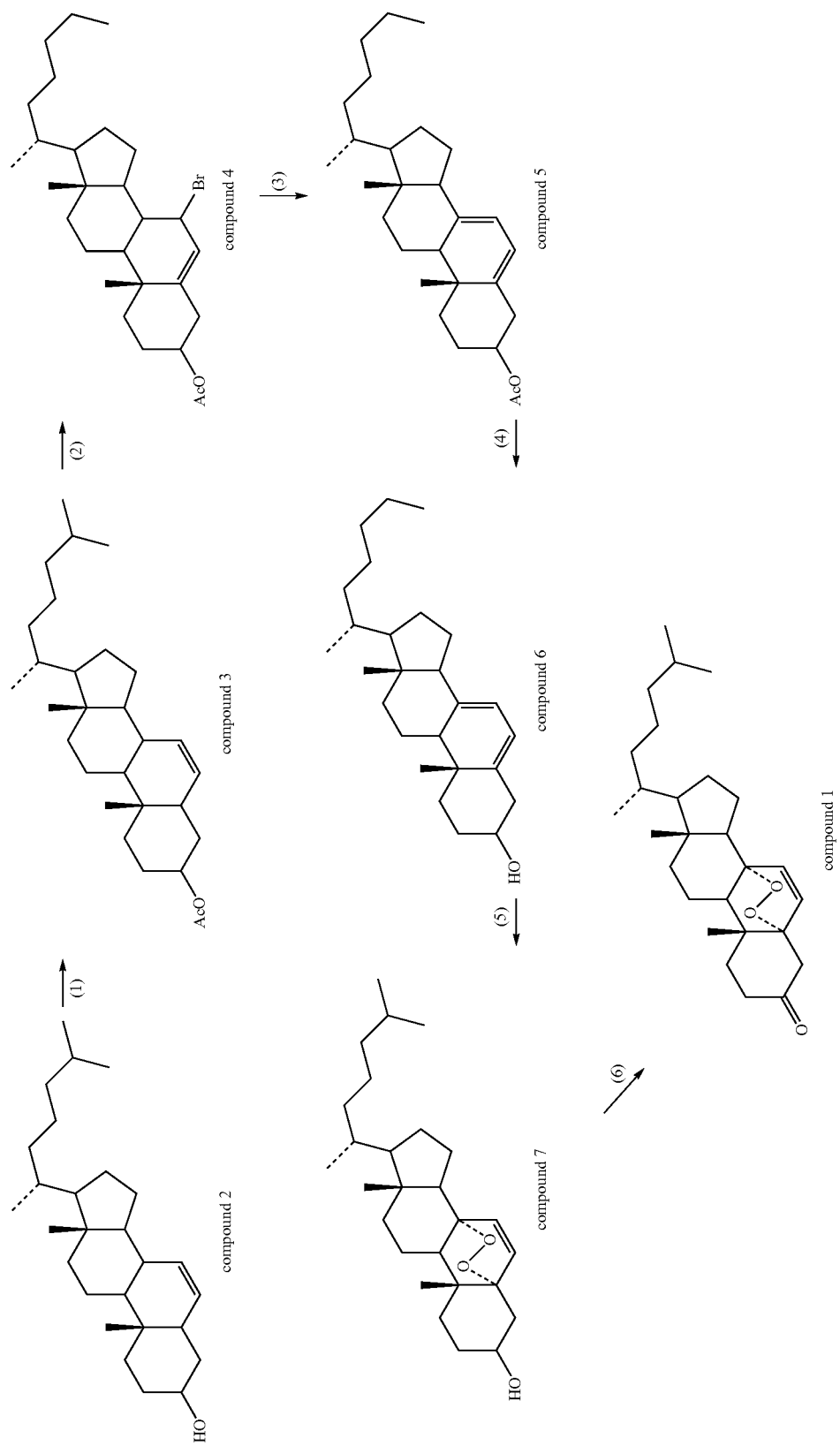

Wherein in the step (1), the organic solvent is selected from a group consisting of following compounds each containing 2-20 carbons: an ether, an alcohol, an alkane, an aromatic hydrocarbon, a ketone, an alkyl halide, an amide, an nitrile, an ester, or a mixture thereof with various mixing ratios; the temperature is from −20° C. to 250° C.; the catalyst is a protonic acid, such as sulphuric acid, or an organic base, such as pyridine; the molar ratio of Compound 2 to the acetic anhydride is 1:1-20.

Wherein in the step (2), the organic solvent is selected from a group consisting of following compounds each containing 1-20 carbons: an aromatic hydrocarbon, an alkane, an ether, a ketone, an alkyl halide, an amide, an nitrile, an ester, or a mixture thereof with various mixing ratios; the temperature is from −10° C. to 150° C.; the bromide reagent is bromosuccinimide (NBS), hydrogen bromide, or acetyl bromide; the catalyst is triphenylphosphine or a light source with a wavelength of 290-800 nm; the molar ratio of Compound 3 to the bromide reagent is 1:1-10.

Wherein in the step (3), the organic solvent is selected from a group consisting of following compounds each containing 1-20 carbons: an aromatic hydrocarbon, an alkane, an ether, a ketone, an alkyl halide, an amide, an nitrile, an ester, or a mixture thereof with various mixing ratios; the temperature is from 0° C. to 150° C.; the catalyst is an organic base, such as pyridine or triethylamine; the molar ratio of Compound 4 to the organic base is 1:1-10.

Wherein in the step (4), the organic solvent is selected from a group consisting of following compounds each containing 2-20 carbons: an ether, an alcohol, an alkane, an aromatic hydrocarbon, a ketone, an alkyl halide, an amide, an nitrile, an ester, or a mixture thereof with various mixing ratios; the temperature is from 0° C. to 150° C.; the catalyst is a protonic acid with the represent of sulphuric acid, or a protonic base with the represent of sodium hydroxide.

Wherein in the step (5), the organic solvent is selected from a group consisting of following compounds each containing 1-20 carbons: an aromatic hydrocarbon, an alkane, an ether, a ketone, an alkyl halide, an amide, an nitrile, an ester, or a mixture thereof with various mixing ratios; the temperature is from 0° C. to 150° C.; the catalyst is Eosin Y, triphenylphosphine, or a light source with a wavelength of 290-800 nm.

Wherein in the step (6), the organic solvent is selected from a group consisting of following compounds each containing 1-20 carbons: an aromatic hydrocarbon, an alkane, an ether, a ketone, an alkyl halide, an amide, an nitrile, an ester, or a mixture thereof with various mixing ratios; the temperature is from −20° C. to 100° C.; the sulphuric acid or chromic acid solution is the representative of the oxidant.

The compound CL168 represented by the general structural formula II can be prepared by a method including the following steps:

(1) dissolving cholesterol (Compound 2) in an organic solvent to produce Compound 3 by reacting the cholesterol with a R-donating reagent (R represents a $C_{2-25}$ alkyl group, aryl group, aryl group substituted with electron-donating group or electron withdrawn group, $C_{3-6}$ alkynyl group, alkenyl group, $C_{3-9}$ cycloalkyl group, $C_{3-9}$ substituted heterocycloalkyl group, $C_{1-20}$ fatty acyl group, aromatic acyl group, sulfonyl, cinnamoyl, caffeoyl, galloyl, feruloyl, benzoyl, L-aliphatic amino acyl, or L-aromatic amino acyl) under the catalysis of a catalyst, at a certain temperature;

(2) dissolving the Compound 3 in an organic solvent to produce Compound 4 by reacting Compound 3 with a bromide reagent under the catalysis of a catalyst, at a certain temperature;

(3) dissolving the Compound 4 in an organic solvent to produce Compound 5 by elimination reaction with a base at a certain temperature;

(4) dissolving the Compound 5 in an organic solvent to produce Compound 6 by oxidizing the compound 5 with an oxidant at a certain temperature;

The reaction equations in the above-mentioned steps (1)-(4) are as follows:

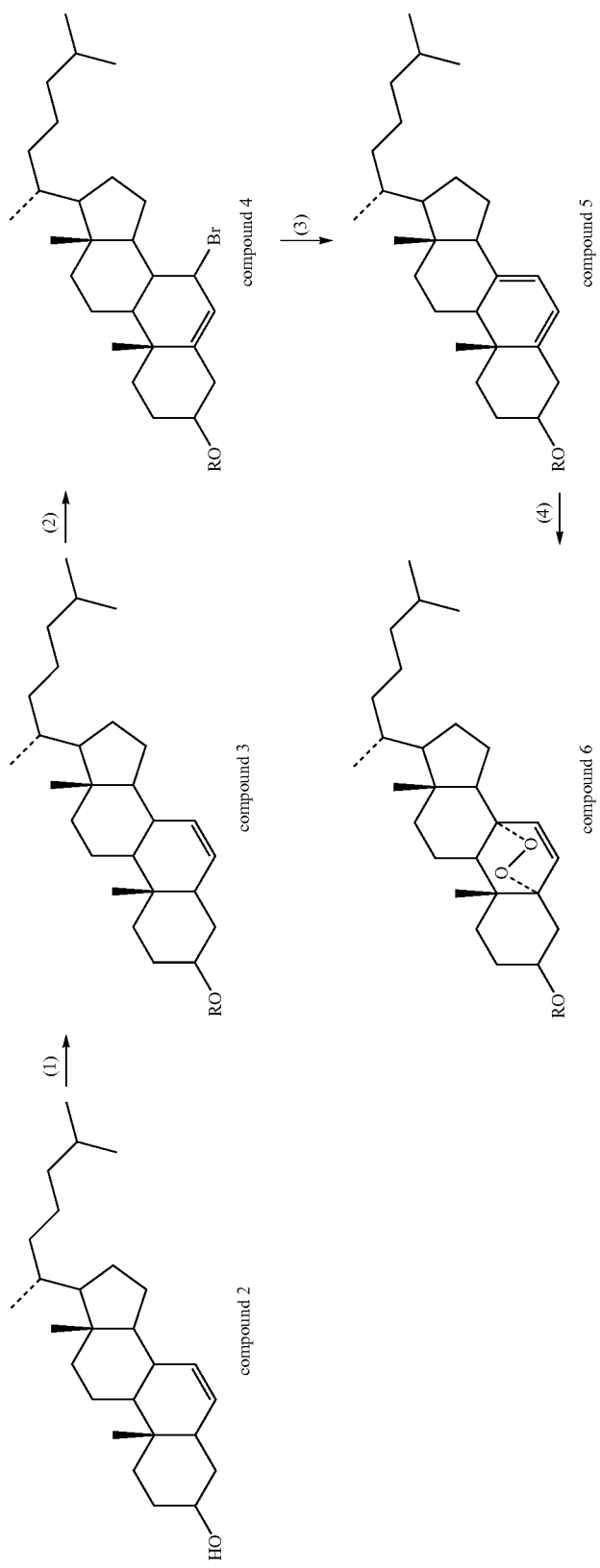

Wherein in the step (1), the organic solvent is selected from a group consisting of following compounds each containing 2-20 carbons: an ether, an alcohol, an alkane, an aromatic hydrocarbon, a ketone, an alkyl halide, an amide, an nitrile, an ester, or a mixture thereof with various mixing ratios; the temperature is from −20° C. to 250° C.; the catalyst is a protonic acid, such as sulphuric acid, or an organic base, such as pyridine; the molar ratio of Compound 2 to the acetic anhydride is 1:1-20;

Wherein in the step (2), the organic solvent is selected from a group consisting of following compounds each containing 1-20 carbons: an aromatic hydrocarbon, an alkane, an ether, a ketone, an alkyl halide, an amide, an nitrile, an ester, or a mixture thereof with various mixing ratios; the temperature is from −10° C. to 150° C.; the bromide reagent is bromosuccinimide (NBS), hydrogen bromide, or acetyl bromide; the catalyst is triphenylphosphine or a light source with a wavelength of 290-800 nm; the molar ratio of Compound 3 to the bromide reagent is 1:1-10;

Wherein in the step (3), the organic solvent is selected from a group consisting of following compounds each containing 1-20 carbons: an aromatic hydrocarbon, an alkane, an ether, a ketone, an alkyl halide, an amide, an nitrile, an ester, or a mixture thereof with various mixing ratios; the temperature is from 0° C. to 150° C.; the catalyst is an organic base with the Z represents of pyridine and triethylamine; the molar ratio of Compound 4 to the organic base is 1:1-10;

Wherein in the step (4), the organic solvent is selected from a group consisting of following compounds each containing 1-20 carbons: an aromatic hydrocarbon, an alkane, an ether, a ketone, an alkyl halide, an amide, an nitrile, an ester, or a mixture thereof with various mixing ratios; the temperature is from 0° C. to 150° C.; the catalyst is Eosin Y, triphenylphosphine, or a light source with a wavelength of 290-800 nm;

The above-obtained CL168-6 (5α,8α-cyclicobioxygen-6-cholesten-3-one) has significant inhibition effect on the proliferation of the human hepatoma cell HepG2 and the human lung cancer cell A549 in vitro;

The above-obtained CL168-6 (5α,8α-cyclicobioxygen-6-cholesten-3-one) has significant inhibitory activity on tumor angiogenesis;

The above-obtained CL168-6 (5α,8α-cyclicobioxygen-6-cholesten-3-one) can effectively inhibit the growth of the tumor S180, prolong the survival time of tumor-bearing mice, and increase the spleen index of the mice;

The above-obtained CL168-6 (5α,8α-cyclicobioxygen-6-cholesten-3-one) shows low toxicity in vivo, and the $LD_{50}$ of mice is 1479 mg/kg;

The above-obtained CL168-6 (5α,8α-cyclicobioxygen-6-cholesten-3-one) can be made into dosage forms of oral, injection and external administration, and used for the prevention and treatment of tumor.

DETAILED DESCRIPTION OF THE PREFERRED EMBODIMENTS

Figure 1:
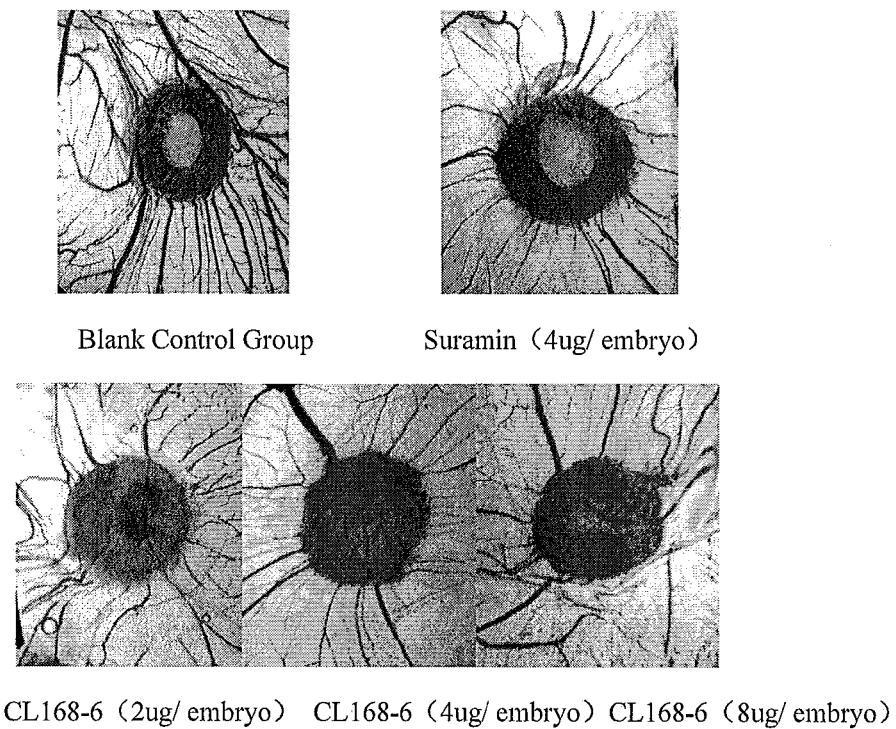
FIG. 1 illustrates the effect of CL168-6 on CAM vessels.

Without limitation, some examples of the present invention will be described by way of illustration hereinafter.

Preparation Example 1

Synthesis of Cholesteryl Acetate (Compound 3)

Cholesterol (11.58 g, 30.00 mmol), toluene (60 ml), acetic anhydride (5.67 ml, 60.00 mmol) and pyridine (1 ml, 12.41 mmol) were placed in a reaction flask of 100 ml, magnetic stirred, heated to 114° C., refluxed and reacted till no raw material is left. The reaction liquid was cooled, washed twice with 2 times amount of hydrochloric acid solution (0.10%), washed twice with 2 times amount of saturated sodium chloride solution, washed twice with 2 times amount of distilled water, dried by anhydrous sodium sulfate, then subjected to vacuum distillation to recover toluene, finally a white solid (12.84 g) was obtained. The yield is 100.0%, and the hydrogen and carbon NMR spectra of Compound 3 are as follows:

$^1$HNMR (500 MHZ, CDCl$_3$): 0.68 (s, 3H, H-18), 0.86 (d, 3H, J=2 HZ, H-26), 0.87 (d, 3H, J=2 HZ, H-27), 0.91 (d, 3H, J=4.4 HZ, H-21), 1.02 (s, 3H, H-19), 2.03 (s, 3H, H-2'), 2.32 (dd, 2H, H-4), 4.60 (m, 1H, H-3), 5.39 (t, 1H, H-6);

$^{13}$CNMR (500 MHZ, CDCl$_3$): 36.6 (C-1), 31.9 (C-2), 74.0 (C-3), 39.7 (C-4), 140.0 (C-5), 122.7 (C-6), 28.2 (C-7), 31.8 (C-8), 50.0 (C-9), 38.1 (C-10), 21.0 (C-11), 37.0 (C-12), 42.3 (C-13), 56.1 (C-14), 24.3 (C-15), 27.8 (C-16), 56.7 (C-17), 11.9 (C-18), 19.3 (C-19), 35.8 (C-20), 18.7 (C-21), 36.2 (C-22), 23.8 (C-23), 39.5 (C-24), 28.0 (C-25), 22.6 (C-26), 22.8 (C-27), 170.6 (C-1'), 21.5 (C-2').

Preparation Example 2

Synthesis of 7-dehydrocholesten-3-ol acetate (Compound 5)

Cholesteryl acetate (4.28 g, 10.00 mmol), carbon tetrachloride (30 ml) and NBS (1.78 g, 10.00 mmol) were placed in a reaction flask of 50 ml, exposed to fluorescent light, refluxed at 74° C. and reacted till no raw material is left. The reaction liquid was cooled, subjected to air pump filtration, washed with a little amount of carbon tetrachloride, subjected to vacuum distillation to recover carbon tetrachloride, finally an orange-yellow, oil-like liquid was obtained.

The orange-yellow, oil-like liquid was added to toluene (50 ml) and 2,6-dimethylpyridine (5 ml), placed in a reaction flask of 100 ml, magnetic stirred, heated to 114° C., refluxed and reacted till no raw material is left. The reaction liquid was cooled, washed twice with 2 times amount of hydrochloric acid solution (0.10%), washed twice with 2 times amount of saturated sodium chloride solution, washed twice with 2 times amount of distilled water, dried by anhydrous sodium sulfate, then subjected to vacuum distillation to recover toluene, dissolved in absolute ethyl alcohol, subjected to repeated crystallization to obtain 3.54 g of a white solid, with a yield of 85.5%. The hydrogen and carbon NMR spectra of Compound 5 are as follows:

$^1$HNMR (500 MHZ, CDCl$_3$): 0.62 (s, 3H, H-18), 0.87 (d, 3H, J=2 HZ, H-26), 0.87 (d, 3H, J=2 HZ, H-27), 0.94 (d, 3H, J=4.4 HZ, H-21), 0.99 (s, 3H, H-19), 2.04 (s, 3H, H-2'), 2.38

(m, 1H, H-4-a), 2.50 (m, 1H, H-4-b) 4.70 (m, 1H, H-3), 5.39 (d, 1H, J=2 HZ, H-7), 5.59 (d, 1H, J=2 HZ, H-6)

$^{13}$CNMR (500 MHZ, CDCl$_3$): 36.6 (C-1), 28.1 (C-2), 72.8 (C-3), 37.9 (C-4), 141.6 (C-5), 120.2 (C-6), 116.2 (C-7), 138.5 (C-8), 46.0 (C-9), 39.5 (C-10), 21.5 (C-11), 37.1 (C-12), 42.9 (C-13), 55.4 (C-14), 23.9 (C-15), 28.1 (C-16), 55.8 (C-17), 11.8 (C-18), 18.4 (C-19), 36.2 (C-20), 16.2 (C-21), 36.1 (C-22), 23.0 (C-23), 39.1 (C-24), 28.1 (C-25), 22.6 (C-26), 22.8 (C-27), 170.6 (C-1'), 21.0 (C-2').

Preparation Example 3

Synthesis of 7-dehydrocholesterol (Compound 6)

7-dehydrocholesten-3-ol acetate (Compound 5) (2.07 g, 5 mmol), ethanol (50 ml) and sodium hydroxide solution (10%, 50 ml) were placed in a reaction flask of 250 ml, reacted at 80° C. till no raw material is left. The reaction liquid was subjected to vacuum distillation to recover the remained ethanol, extracted once with one time amount of ethyl acetate, washed with distilled water to neutral, and dried by anhydrous sodium sulfate. After recovering of ethyl acetate, the resulting solid was subjected to repeated crystallization with ethanol to obtain 1.85 g of 5,7-diene cholesterol, with a yield of 96.4%. The hydrogen NMR spectrum of Compound 6 is as follows:

$^1$HNMR (500 MHZ, CDCl$_3$): 0.62 (s, 3H, H-18), 0.86 (d, 3H, J=2 HZ, H-26), 0.88 (d, 3H, J=2 HZ, H-27), 0.94 (s, 3H, H-19), 1.22 (d, 3H, J=12 HZ, H-21), 2.33 (dd, 1H, H-4-a), 2.49 (dd, 1H, H-4-b), 3.66 (m, 1H, H-3), 4.03 (m, 1H, 3-OH), 5.39 (m, 1H, H-7), 5.68 (dd, 1H, H-6).

Preparation Example 4

Synthesis of 5α,8α-cyclicobioxygen-6-cholesten-3-ol (Compound 7)

5,7-diene cholesterol (1.15 g, about 3 mmol), Eosin Y (200 mg, about 0.31 mmol, dissolved in alcohol) and absolute ethanol (100 ml, 10.00 mmol) were placed in a reaction flask of 250 ml. After blowing air into the reaction liquid, the latter was exposed to fluorescent light, reacted till no raw material is left, distilled to recover the absolute ethanol until a certain volume is achieved, stood for crystallization to obtain 0.94 g of 5α, 8α-cyclicobioxygen-6-cholesten-3-ol, with a yield of 75.3%.

$^1$HNMR (500 MHZ, CDCl$_3$): 0.80 (s, 3H, H-18), 0.85 (d, 3H, J=2 HZ, H-26), 0.88 (d, 3H, J=2 HZ, H-27), 0.88 (s, 3H, H-19), 0.91 (d, 3H, J=12 HZ, H-21), 3.97 (m, 1H, H-3), 6.23 (d, 1H, J=7 HZ, H-7), 6.51 (d, 1H, J=7 HZ, H-6);

$^{13}$CNMR (500 MHZ, CDCl$_3$): 36.0 (C-1), 28.3 (C-2), 66.5 (C-3), 39.4 (C-4), 82.2 (C-5), 135.4 (C-6), 130.8 (C-7), 79.5 (C-8), 51.1 (C-9), 35.2 (C-10), 20.6 (C-11), 34.7 (C-12), 44.8 (C-13), 52.0 (C-14), 23.4 (C-15), 30.1 (C-16), 56.4 (C-17), 12.7 (C-18), 18.2 (C-19), 36.9 (C-20), 19.0 (C-21), 36.9 (C-22), 23.8 (C-23), 37.0 (C-24), 28.0 (C-25), 22.6 (C-26), 22.8 (C-27).

Preparation Example 5

Synthesis of 5α,8α-cyclicobioxygen-6-cholesten-3-one (Compound 1, CL168-6)

5α,8α-cyclicobioxygen-6-cholesten-3-ol (Compound 7) (0.62 g, about 1.5 mmol) was dissolved in acetone (50 ml) in a reaction flask of 100 ml, slowly added by drops of chromic acid solution (1.6 mmol) under ice-water bath, reacted till no raw material is left. The reaction liquid was poured into an ice-water mixture (600 ml), stirred, stood for a whole night, and then subjected to air pump filtration. The filter cake was subjected to repeated crystallization with ethanol to obtain 0.62 g of 5α,8α-cyclicobioxygen-6-cholesten-3-one, with a yield of 96.1%.

$^1$HNMR (500 MHZ, CDCl$_3$): 0.85 (s, 3H, H-19), 0.88 (d, 3H, J=2 HZ, H-26), 0.89 (d, 3H, J=2 HZ, H-27), 0.92 (d, 3H, J=6.5 HZ, H-21), 1.07 (s, 3H, H-18), 3.97 (m, 1H, H-3), 6.29 (d, 1H, J=8.5 HZ, H-7), 6.59 (d, 1H, J=8.5 HZ, H-6);

$^{13}$CNMR (500 MHZ, CDCl$_3$): 36.7 (C-1), 35.3 (C-2), 207.0 (C-3), 43.6 (C-4), 83.4 (C-5), 134.2 (C-6), 131.6 (C-7), 80.0 (C-8), 51.1 (C-9), 39.4 (C-10), 20.5 (C-11), 37.3 (C-12), 44.9 (C-13), 51.4 (C-14), 23.8 (C-15), 28.2 (C-16), 56.4 (C-17), 12.8 (C-18), 18.5 (C-19), 35.2 (C-20), 17.5 (C-21), 35.9 (C-22), 23.5 (C-23), 39.3 (C-24), 28.0 (C-25), 22.5 (C-26), 22.8 (C-27).

Resulting Example 1

Assessment of the Effect of CL168-6 on the Proliferation of a Human Hepatoma Cell HepG2, a Human Lung Cancer Cell A549 and a Human Immortalized Fibroblast Cell NIH3T3 Through MTT Assay 1. Materials
1.1 Tumor Strains The human hepatoma cells HepG2 and the human lung cancer cells A549 were cultivated by the PLA Institute of Infectious Disease to assume the viability, while the human immortalized fibroblast cells NIH3T3 were bought from the Academy of Military Medical Sciences.

1.2 Experimental Drugs

CL168-6, prepared by ourselves, which had a purity of equal to or more than 98% evaluated by High Pressure Liquid Chromatography (HPLC) and therefore met the experimental requirements. The powder of said CL168-6, which had been previously sealed and stored in 4° C., was dissolved in dimethyl sulfoxide (DMSO) to obtain a stock solution of 1 ml/mg for later use.

2. Method
2.1 Cell Cultivation

The human hepatoma cells HepG2, human lung cancer cells A549 and NIH3T3 cells were recovered, and subcultured in culture flasks. Once the cells grew to the logarithmic phase, the experiment can be started. The cells were digested by high-pressure filtered trypsin to prepare a cell-containing suspension, dyed for 3 minutes with 0.4% trypan blue, and then counted with the blood-cell counter (living cells were not colored, while dead cells were stained blue). The percentages of living cells evaluated by trypan blue exclusion were all up to more than 98%.

2.2 Experiments on Inhibition of Cell Multiplication

The three types of cells in logarithmic phase were seeded in 96-well plates with a density of 1×10$^4$/ml (200 μL/well), and then cultivated for 24 hours at 37° C. in 5% CO$_2$ cultivable box. The culture media was aspirated and discarded. 200 ul CL168-6 solutions of different concentration (with a final concentration respectively of 10 μg, 5 μg, 2.5 μg and 0 μg/mL prepared with a culture medium of 4% calf serum in DMEM) were added, wherein for each concentration there were 6 parallel wells. After cultivating for 24 hours and 48 hours, 100 ul supernatant was carefully aspirated and discarded, respectively. MTS (20 μl/well) was added and mixed evenly. The mixture was cultivated for 1 hour at 37° C. in 5% CO$_2$ cultivable box. The absorbency at 492 nm was determined by quantitative Enzyme-linked immunosorbent assay (ELISA). The experiment was repeated for three times. The growth inhibition rate was calculated as follows.

Growth Inhibition rate(%)=[(mean OD value of control group−mean OD value of treatment group)/mean OD value of control group]×100%

3. Results

CL168-6 has a significant inhibition effect on the proliferation of the human hepatoma cell HepG2 and the human lung cancer cell A549 cultivated in vitro, and shows dose-dependent; the relevant results are listed in Table 1-1. When treated by the drug with a concentration of 2.5 μg/ml for 24 hours, the inhibition rate is 52.85% and 48.69% respectively for HepG2 cells and A549 cells. The inhibition rate will increase with the increasing of the drug concentration; when the drug concentration is 10 μg/ml, the inhibition rate to the above two types of cells is respectively up to 64.39% and 62.40%; when after 48 hours and the dosage is 2.5 μg/ml, the inhibition rate to HepG2 and A549 cells is respectively up to 59.83% and 51.91%; when the concentration is 10 the rate to HepG2 and A549 is respectively 73.67% and 69.67%. Compared with the situation of NIH3T3 cells, the inhibition of CL168-6 to HepG2 and A549 shows significant difference in groups with different concentration and treatment time ($p<0.05$). The experimental results show that the inhibition effect of CL168-6 to cells has a good selectivity, and the effect is positive correlated to the drug concentration and medication time.

TABLE 1-1

Inhibition Effect of CL168-6 on the multiplication of 3 types of cell strains

| Concentration (μg/ml) | 24 h Inhibition rate (%) | | | 48 h Inhibition rate (%) | | |
|---|---|---|---|---|---|---|
| | HepG2 | A549 | NIH3T3 | HepG2 | A549 | NIH3T3 |
| 0 | — | — | — | — | — | — |
| 2.5 | 52.85* | 48.69* | 3.87 | 59.83* | 51.91* | 0.75 |
| 5.0 | 58.51* | 55.78* | 5.69 | 69.08* | 59.75* | 1.97 |
| 10.0 | 64.39* | 62.40* | 8.45 | 73.67* | 69.37* | 5.37 |

Notes:
*$P < 0.05$ vs 0.0 μg/ml

4. Conclusion

CL168-6 can significantly inhibit the multiplication of human hepatoma cells HepG2 and human lung cancer cells A549.

Resulting Example 2

Assessment of the Effect of CL168-6 on Tumor Angiogenesis Through CAM Assay

1. Materials
1.1 Animals

German Roman embryonated eggs (each weight 50-60 g, obtained from the Embryo Experimental Center of China Agricultural University).

1.2 Experimental Drugs

CL168-6, prepared by ourselves, which had a purity of equal to or more than 98% evaluated by High Pressure Liquid Chromatography (HPLC) and therefore met the experimental requirements. The powder of said CL168-6 was sealed and stored in 4° C.

Suramin, brought from SIGMA company.

2. Method 2.1 Preparation Method of Samples to be Assessed

A sterile gelatin sponge, previously made into disks with diameter of 5 mm by a hole puncher, was used as sample carrier. CL168-6 was dissolved in 70% ethanol to prepare a solution with a concentration of 2 mg/5 ml. There were 3 dose groups, wherein 5 μl (low dose group, with a dose volume of 2 μg/embryo), 10 μl (middle dose group, with a dose volume of 4 μg/embryo), and 20 μl (high dose group, with a dose volume of 8 μg/embryo) of the solution were added respectively into gelatin sponge slices by a quantitative liquid transfer. The sponge slices were dried in the sterile environment.

2.2 Embryo Incubation and Process for Removing Air Chamber of the Embryo Egg

A sterilized egg was placed into a 37° C. incubator with its air chamber upward. In the $7^{th}$ day, the embryo was positioned on a super-clean bench and sterilized by ethanol, and then it was drilled by a dental drill to form a little hole in the top of the embryo. Egg shell and shell membrane around the hole were carefully removed to form an opening of about 1.2 cm×1.2 cm; after determining a sample-adding site, the air chamber membrane was carefully pricked at the separation place between the chamber and the yolk by a syringe needle; through the prick hole 1-2 drops of sterilized water was injected, which made the chamber membrane and the CAM membrane be separated; after gently removing the upper layer of the chamber membrane with forceps, the CAM membrane in the lower layer was exposed.

2.3 Sample Adding Process

A drug-containing carrier was placed, at the junction area of the CAM membrane and the yolk sac membrane, on a site where vessels were less, and then sealed with sterilized transparent adhesive tape to continue to incubate for 72 hours.

2.4 Vessels Measurement

After the incubation, the transparent adhesive tape stopped on the top of the air chamber was gently removed by forceps; a mixture of methanol/acetone (1:1, 1-2 ml) was gently added; the room temperature was remained constant for 10 minutes. Then, the CAM membrane was carefully peeled off and placed on a glass slide for observing and taking photos. The effect of the compound on angiogenesis was assessed by counting the numbers of large, middle, small blood vessels radiated by the carrier.

2.5 Statistical Treatment

All the data were statistical analyzed by SPSS 11.0 software package; the comparison of the counting data was verified by $x^2$ test. Since $P<0.05$, all had statistical significance.

3. Results

FIG. 1 illustrates the effect of CL168-6 on CAM vessels and the blank control.

The numbers of minute vessels of the three dose groups of CL168-6 are compared with that of the blank group respectively; for all the three groups significant differences are found, and dose-dependent is showed. The results are listed in Table 2-1, which indicate that the compound has a certain inhibition effect on the growth of angiogenesis.

TABLE 2-1

Statistical Table about Effect of CL168-6 on CAM vessels with analysis of Vessels [$\overline{X}$ (number of the vessels) ± S]

| Groups | Number of embryos | Large vessels | Middle vessels | Small vessels |
|---|---|---|---|---|
| CL168-6 (2 ug/embryo) | 20 | 3.5 ± 1.8 | 13.2 ± 3.7 | 8.8 ± 2.3** |
| CL168-6 (4 ug/embryo) | 20 | 3.6 ± 1.9 | 11.2 ± 3.2 | 6.5 ± 2.5** |
| CL168-6 (8 ug/embryo) | 20 | 2.5 ± 2.0 | 12.6 ± 5.6 | 4.0 ± 2.8** |
| Suramin (4 ug/embryo) | 20 | 3.6 ± 2.0 | 12.4 ± 3.8 | 6.1 ± 3.0** |
| Blank control group | 20 | 4.7 ± 3.1 | 18.1 ± 5.5 | 11.6 ± 2.2 |

Notes:
compared with the blank control group, *P < 0.05, **P < 0.01.

4. Conclusion

CL168-6 has a significantly inhibition effect on tumor angiogenesis, and said effect is dependent on the amount of the drug.

Resulting Example 3

Anti-Tumor Effect of CL168-6 to Tumor-Bearing Ascites Mice S180, H22

1. Materials 1.1 Experimental Animals and Tumor Strains

Healthy female Balb/C mice, each weight 18-22 g, were bought from Experimental Animal Center of the Academy of Military Medical Sciences (Certification No. SCXK-(Military) 2007-004). Mouse hepatoma cells H22 was cultivated by our laboratory to assume the viability; mouse sarcoma cells S180 were presented by the Institute of Chinese Medicine of 302 Hospital; tumor-bearing ascites mice S180, H22 were subcultured once every 7 days.

1.2 Experimental Drugs

CL168-6, prepared by ourselves, which had a purity of equal to or more than 98% evaluated by High Pressure Liquid Chromatography (HPLC) and therefore met the experimental requirements. The powder of said CL168-6 was sealed and stored in 4° C.

Cyclophosphamide for Injection: manufactured by Shanxi Pude Pharmaceutical Co., Ltd.

2. Process 2.1 Establishment of Animal Models

Ascites mice S180 and H22 that had been vaccinated 7 days were sacrificed by cervical, from which ascites were obtained under sterile conditions respectively; the obtained ascites were washed twice with culture medium RPMI1640, and prepared to a $2\times10^7$/ml suspension in sterile physiological saline. The suspension of cell S180 was inoculated subcutaneously in the right axillas of 40 mice (0.1 ml/mouse) to produce solid tumor models; while the suspension of cell H22 was inoculated in abdominal cavities of 40 mice (0.2 ml/mouse) by conditional means under sterile conditions to produce ascites tumor models.

2.2 Experimental Groups 90 mice were randomly divided into 9 groups of 3 types, wherein the first type group was a normal control group, the second type groups were S180 solid tumor groups including a positive (cyclophosphamide) control group, a negative control group, a low dose group and a high dose group, and the third type groups were H22 ascites groups including a positive (cyclophosphamide) control group, a negative control group, a low dose group and a high dose group. There were 10 mice in each group. The experiment was repeated for three times.

2.3 Drug Administration

CL168-6 was prepared as emulsions in corn oil. The low dose group was injected with the dose of 16 mg/kg, the high dose group was injected with the dose of 32 mg/kg, the negative control group was injected same volume of corn oil, and the positive control group was injected cyclophosphamide injection solution with the dose of 0.02 g/(Kg.d). The used injection volume was 0.1 ml/mouse and the injection was given as intraperitoneal injection every other day for 15 days. During the 15 days, general activities, fur, feces, etc. of the mice were daily observed. 24 hours after the last administration, mice that had been inoculated subcutaneously with S180 were sacrificed by cervical, from which tumors, thymus and spleen were taken out. After the last administration, mice that had been inoculated in abdominal cavities with H22 were conventionally bred continually, weighted and observed the survival time every day until all the mice in the negative group were dead.

2.4 Calculation of Survival Extending Rate of Mice 24 hours after the inoculation of ascites, the weight and the amount of abdominal circumference of the mice in the groups of ascites models were measured. The drug administration and breeding were continued according to different groups, the weight and the abdominal circumference were measured daily until one day before death. The weight increase (g) and abdominal-circumference increase (cm) were calculated. The experiment started on the day of tumor inoculation and ended on the day when all the mice in the negative control group were dead; the time of deaths were recorded, and the survival extending rate was calculated.

Survival Extending Rate(%)=[(mean survival days of treatment group−mean survival days of negative control group)/mean survival days of control group]×100%

2.5 Calculation of Spleen Index and Liver Index

After finishing the administration in all mice in the solid tumor group, the mice were sacrificed and their spleens and livers were weighed by electronic balance. The spleen index was equivalent to the spleen weight (mg) of mice in each group divided by the weight of the mice, while the liver index was equivalent to the liver weight (100 g) divided by the weight (g) of the mice.

2.6 Calculation of Tumor Inhibition Rate

On the next day after drug withdrawal, the mice in the solid-tumor negative-control group were weighed and sacrificed by cervical, wherein the serum was collected by eye bleeding for later use in subsequent experiments. Tumor tissues were dissected and weighed by electronic balance. The tumor inhibition rate was calculated as follows.

Tumor Inhibition Rate(%)=[(mean tumor weight of negative control group−mean tumor weight of treatment group)/mean tumor weight of control group]×100%

2.7 Statistical Treatment

All the data were statistical analyzed by SPSS 11.0 software package; the comparison of the counting data was verified by $x^2$ test. Since $P<0.05$, all had statistical significance.

3. Experimental Results

Figure 2:
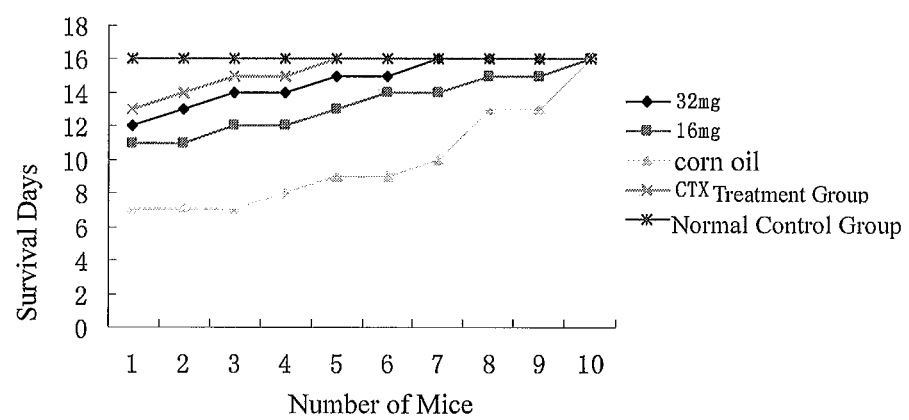
FIG. 2 shows survival curves of mice.

3.1 Change of Weight, Abdominal Circumference and Survival Time of Mice in the Groups As shown in Table 3-1, mice in CL168-6 low and high dose groups had longer survival time than that in the negative control group, and the relevant survival extending rates were 37.11% and 51.55%, respectively. The mice in the treatment group had a smaller increase of abdominal circumference than that in the negative group, and the normal growth of those treated mice wasn't affected by said increase. The weight of mice in the cyclophosphamide injected group increased slowly, only had an increase of 3.42 g, while the mice in the normal group had a weight increase of 6.72 g. FIG. 2 illustrates a statistical chart on survival time of H22 ascites mice.

TABLE 3-1

Effect of CL168-6 on weight, abdominal circumference and survival time of mice in various groups (x ± s)

| Groups | Weight increase (g) | Abdominal circumference increase (cm) | Survival time (day) | Survival extending rate (%) |
| --- | --- | --- | --- | --- |
| Normal control group | 6.76 ± 1.56 | 0.58 ± 0.09 | — | — |
| Negative control group | 4.85 ± 1.21① | 3.17 ± 0.33② | 9.7 ± 2.7 | — |
| Cyclophosphamide group | 3.42 ± 1.67②④ | 2.30 ± 0.66②④ | 15.3 ± 1.06④ | 57.73 |
| CL168-6 low dose group | 7.16 ± 1.39④ | 2.84 ± 0.34②③ | 13.3 ± 1.77④ | 37.11 |
| CL168-6 high dose group | 5.05 ± 1.88④ | 2.32 ± 0.71②④ | 14.7 ± 1.41④ | 51.55 |

Notes:
1. Compared with the normal control group: ①$P < 0.05$, ②$P < 0.01$;
2. Compared with the negative control group: ③$P < 0.05$, ④$P < 0.01$.

3.2 Change of Liver Index and Spleen Index of Mice in Various Groups

As shown in Table 3-2, both the liver index and the spleen index of the ascites mice in cyclophosphamide group were respectively lower than that of the mice in the negative control group, therefore they had statistical significance. While all the indexes of CL168-6 low and high dose groups were larger than that of the negative control group.

TABLE 3-2

Effect of CL168-6 on liver index and spleen index of ascites mice (x ± s)

| Groups | Liver index (100 g/g) | Spleen index (mg/g) |
| --- | --- | --- |
| Blank control group | 4.04 ± 0.47 | 3.45 ± 0.58 |
| Negative control group | 4.32 ± 0.14 | 3.84 ± 0.56 |
| Cyclophosphamide group | 3.26 ± 0.27①④ | 2.45 ± 0.34①④ |
| CL168-6 low dose group | 4.9 ± 0.24①④ | 6.53 ± 1.29②④ |
| CL168-6 high dose group | 5.19 ± 0.64②④ | 5.76 ± 0.96②④ |

Notes:
1. Compared with the normal control group: ①$P < 0.05$, ②$P < 0.01$;
2. Compared with the negative control group: ③$P < 0.05$, ④$P < 0.01$.

3.3 Anti-Cancer Activity of CL168-6 In Vivo

Figure 3:
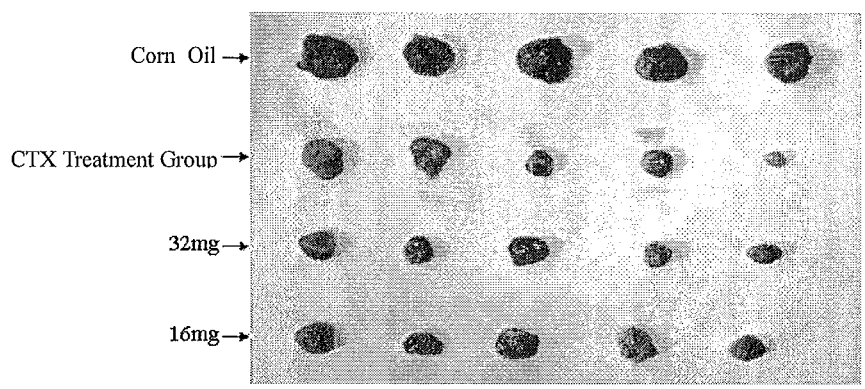
FIG. 3 shows mice tumors of various dose groups.

CL168-6 had no effect on the weight increase of a S180 sarcoma mouse, while the weight increase of mice in the positive control group was a little small. The tumor inhibition rates of the tumor-bearing S180 sarcoma mice in the low and high dose group were 44.33% and 54.58% respectively; and compared with the negative control group, the high dose group had statistical significance. The results are shown in Table 3-3. Tumor bodies of mice in all the groups are illustrated in FIG. 3.

TABLE 3-3

Inhibition Effect of CL168-6 on S180 sarcoma of mice (x ± s)

| Groups | Weight increase (g) | Tumor weight (g) | Tumor inhibition rate (%) |
|---|---|---|---|
| Blank control group | 6.76 ± 1.56 | — | — |
| Negative control group | 6.92 ± 1.23 | 1.385 ± 0.440 | — |
| Cyclophosphamide group | 4.76 ± 1.01①③ | 0.518 ± 0.231④ | 62.63% |
| CL168-6 low dose group | 6.71 ± 1.22 | 0.771 ± 0.407 | 44.33% |
| CL168-6 high dose group | 6.00 ± 1.11 | 0.629 ± 0.133③ | 54.58% |

Notes:
1. Compared with the normal control group: ①$p < 0.05$, ②$p < 0.01$;
2. Compared with the negative control group: ③$p < 0.05$, ④$p < 0.01$.

3.4 Change of Liver and Spleen Indexes of S180 Mice in the Groups

As shown in Table 3-4, the liver and spleen indexes of the S180 mice in the cyclophosphamide group are lower than that of the negative group, and therefore have statistical significance. While the spleen indexes of mice in the CL168-6 low and high dose groups are higher than that of mice in the negative group, and there is significant difference therebetween; however, there is no significant difference between the relevant liver indexes.

TABLE 3-4

Effect of CL168-6 on spleen index and liver index of S180 mice (x ± s)

| Groups | Liver index (100 g/g) | Spleen index (mg/g) |
|---|---|---|
| Blank control group | 4.04 ± 0.47 | 3.45 ± 0.58 |
| Negative control group | 4.21 ± 0.45 | 3.83 ± 0.63 |
| Cyclophosphamide group | 3.09 ± 0.31①④ | 2.76 ± 0.64①④ |
| CL168-6 low dose group | 4.45 ± 0.19 | 5.32 ± 0.68②④ |
| CL168-6 high dose group | 4.38 ± 0.13 | 5.34 ± 0.73②④ |

Notes:
1. Compared with the normal control group: ①$p < 0.05$, ②$p < 0.01$;
2. Compared with the negative control group: ③$p < 0.05$, ④$p < 0.01$.

4. Conclusion 4.1 CL168-6 can Significantly Inhibit the Growth of S180 Mouse Sarcoma.

4.2 CL168-6 can Improve the Spleen Index of a Tumor-Bearing Mouse.

4.3 CL168-6 can Extend the Survival Time of a Tumor-Bearing Mouse.

4.4 CL168-6 can Dissipate the Ascites or Delay the Ascites Generating in a H22 Mouse.

Resulting Example 4

Research on Anti-Tumor Mechanism of CL168-6

It has been a hot topic in tumor treatment research to study the mechanisms of tumor cell apoptosis and signal transduction, selectively block the signaling pathways of tumor cells, and destroy their self-controlling growth regulatory mechanisms. P53, Bcl-2, P21, VEGF are crucial molecules in the growth or apoptosis of tumor cells. The instant experiment studied the CL168-6 anti-tumor mechanism at molecular level.

I. Experimental Materials (For the details, please refer to Resulting Examples 1 and 3)

II. Experimental Process

1. Detecting VEGF in mouse-eye serum (For the details, please refer to Resulting Examples 1 and 3)

Before taking tumors out, blood was collected by eye bleeding from mice in the four groups, i.e. the negative control group, the positive CTX control group, the high dose (32 mg/kg) group and the low dose (16 mg/kg) group.

1.1 Preparing reagents, samples and standards;

1.2 Adding the prepared samples and standards, and reacting for 90 minutes at 37° C.;

1.3 Washing the plate twice, adding biotinylated antibody working solution, and reacting for 60 minutes at 37° C.;

1.4 Washing the plate for three times, adding ABC working solution, and reacting for 30 minutes at 37° C.;

1.5 Washing the plate for five times, adding TMB color liquid, and reacting in dark for 15 minutes at 37° C.;

1.6 Adding TMB stop solution, and measuring OD value at 450 nm.

2. Determination of activity of Caspase 3, 8, 9

2.0 μg/ml CL168-6 worked on HepG2 cells for 24 hours and 48 hours.

2.1 Collecting samples 2.1.1 HepG2 cells were digested by trypsin in the cell culture medium. The resulting mixture (6000 was centrifuged for 5 minutes at 4° C. to collect the cells. The supernatant was carefully aspirated and discarded. The remains were washed once with PBS, added to lysate (100 μl/2×10$^6$ cells); and then, after resuspending the precipitation, ice cracked for 15 minutes.

2.1.2 The resulting mixture (16000 g) was centrifuged at 4° C. for 15 minutes.

2.1.3 The supernatant was transferred into a centrifugal tube that was pre-cooled by ice bath.

2.2 Detection of Caspase 3 activity 2.2.1 Took out pNA and a suitable amount of Ac-DEVD-PNA (2 mM), put them on the ice bath for later use;

2.2.2 The reaction system was as follows:

| | Blank control | Samples |
|---|---|---|
| Detected buffer solution | 90 μl | 80 μl |
| Samples to be detected | 0 μl | 10 μl |
| Ac-DEVD-PNA(2 mM) | 10 μl | 10 μl |
| Total volume | 100 μl | 100 μl |

2.2.3 Incubating at 37° C. for 120 minutes, detecting Caspase 3 with A405;

2.2.4 Adding Ac-IETD-PNA (2 mM) and Ac-LEHD-PNA (2 mM), respectively, for detecting Caspase 8, 9

3. Detecting the activity of tumor cells VEGF, P53, P21, Bcl-2 (taking β-Actin as an internal reference) Using Protein Electrophoresis (Western Blot) Method 3.1 Extraction of total cellular protein A bean sized tumor tissue dissected previously was shredded and put into a pre-cooled tissue grinder. 400 μl tissue lysis solution was added. After 10 minutes carefully grinding, the mixture was transferred into a 1.5 ml centrifugal tube, and then, after intensely vortexing the tube for 15 seconds, the mixture was placed on ice for 10 minutes and repeatedly oscillated. After centrifuging 20 minutes (12000 rpm), the supernatant was collected, transferred into a pre-cooled Eppendorf tube, and then separately charged and frozen stored at −80° C. for detecting the activity level of various antibodies.

3.2 Protein Determination: using BCA protein assay 3.2.1 Preparation of standard series (Table 4-1): Standard in kit was diluted in series according to the specification thereof to prepare standard solutions with concentrations of 2000 μg/ml, 1500 μg/ml, 1000 μg/ml, 750 μg/ml, 500 μg/ml, 250 μg/ml, 125 μg/ml and 25 μg/ml.

TABLE 4-1

Preparation of standards

| Tube No. | Amount of deionized water | Amount of BSA standard | Final concentration of BSA |
|---|---|---|---|
| A | 0 | 300 μl BSA stock solution | 2000 μg/ml |
| B | 125 μl | 375 μl BSA stock solution | 1500 μg/ml |
| C | 325 μl | 325 μl BSA stock solution | 1000 μg/ml |
| D | 175 μl | 175 μl diluent B | 750 μg/ml |
| E | 325 μl | 325 μl diluent C | 500 μg/ml |
| F | 325 μl | 325 μl diluent E | 250 μg/ml |
| G | 325 μl | 325 μl diluent F | 125 μg/ml |
| H | 400 μl | 100 μl diluent G | 25 μg/ml |
| I | 400 μl | 0 | 0 μg/ml |

3.2.2 Preparation of working solution: Solution A and solution B (50:1) were mixed for later use.

3.2.3 The sample to be detected was diluted to 20 fold dilution. 10 μl sample and 10 μl standard were each added into three wells of a 96-well ELISA plate. 200 μl working solution was added and mixed. The mixture was reacted at 37° C. for 30 minutes.

3.2.4 The ELISA plate was taken out, cooled to room temperature, and measured absorbance value at 562 nm. Standard curve was drawn according to the standards, and protein content of the samples to be measured was calculated by using the standard curve.

3.3 Protein electrophoresis 3.3.1 Preparation of protein samples: Suitable amount of each sample was added to 4 protein sample buffer and 1 protein sample buffer, mixed to make each have a volume of 300 μl and a concentration of 3.7 μg/μl, heated 3-5 minutes in hot water for denaturation, centrifuged in short time with high speed, and then stored at −20° C. for later use.

3.3.2 Preparing 12% separation gel and 4% stacking gel and pouring gel: please refer to Table 4-2.

TABLE 4-2

Preparation of separation gel and stacking gel

| | Separation gel (ml) | Stacking gel (ml) |
|---|---|---|
| 30% Acrylamide solution | 4 | 0.5 |
| 1.5 mmol/L Tris (pH 8.8) | 2.5 | — |
| 1.0 mmol/L Tris (pH 6.8) | — | 0.38 |
| 10% SDS | 0.1 | 0.03 |
| Deionized water | 3.3 | 2.1 |
| 10% Ammonium persulfate (AP) | 0.1 | 0.03 |
| 5% TEMED | 0.004 | 0.003 |

When preparing separation gel and stacking gel, in order to prevent the gel from curing too early, TEMED should be added before pouring the gel. Firstly, the separation gel was poured into interlayer of glasses; then the upper gel surface was sealed by distilled water to maintain a flat gel surface. Secondly, when the separation gel was cured and the distilled water was absorbed out, the mixture was washed with distilled water for several times to remove the acrylamide that was not polymerized. Finally, when the distilled water was absorbed out again, a sample application comb was inserted in, with the front edge thereof being 0.5 cm away from the separation gel.

3.3.3 Sample addition: When the gel cured at room temperature, an electrophoretic buffer was poured into a electrophoresis tank; after unplugging a sample loading comb, suitable volumes of samples to be assayed were respectively added into comb wells by micropipette according to the concentrations of cytoplasmic protein.

3.3.4 Electrophoresis: After adding sample, connecting power supply, firstly setting the voltage at 120V and during this period the sample was stacked as a line in the stacking gel and the front edge of the sample entered into the separation gel; then setting the voltage at 100V and during this period conducting constant voltage electrophoresis for 120 minutes; finally, shutting off the power supply when bromophenol blue indicator reached the bottom edge of the gel.

3.4 Analysis on western blot 3.4.1 Electrotransfer: PVDF film was firstly soaked in absolute methanol for 30 seconds to make it be transparent, and then soaked in distilled water for 10 minutes, finally soaked with Whatman paper in transfer buffer. The gel was removed. The filter paper, gel, PVDF film and filter paper were placed in order with avoiding shortcut by ensuring the sizes of both sides of the papers, fixed and inserted into an electrotransfer tank with ensuring the gel in the cathode direction and the PVDF film in the anode direction. The electrotransfer performed for 3 hours at 80V, 4° C.

3.4.2 Sealing: After the electrotransfer, the PVDF film was taken out, sealed by a 5% BSA blocking buffer (resolved in a 1 TBST solution) at room temperature for 3 hours, and then oscillating washed with TBST for 3 times, each for 10 minutes.

3.4.3 Reaction with the first antibody: The first antibody was diluted by TBST solution at a ratio of 1:200, and then reacted with the PVDF film at 4° C. for a night. In the next day, after balanced at room temperature for one hour, the reaction mixture was washed with TBST for 3 times.

3.4.4 Reaction with the second antibody: The corresponding HRP-conjugated second antibody was diluted by TBST solution at a ratio of 1:2000, reacted with the PVDF film at room temperature for 2 hours, and then washed with TBST for 3 times.

3.4.5 Development and fixation: Substrate solutions A and B were mixed at a ratio of 1:1. The mixture was dropped on the PVDF film, incubated 5 minutes at room temperature, and, after the excess liquid on the film was removed, the remaining substances were enclosed with plastic wrap to prevent babbles from existing between the PVDF film and the plastic film. The following procedures included lamination, exposure, development, 1 minute double-distilled water washing, and 1 minute snapshot.

3.4.6 The scanned developing photos were subjected to optical density analysis via the software of Alpha Ease FC4.0, which took the average light intensity of B-actin bands as an inner reference value, and showed the results as a ratio of the corresponding protein levels to β-actin.

4. Statistical Treatment

All the data were statistical analyzed by SPSS 11.0 software package; data of normal distribution and variance homogeneity were studied by t test. If the data did not meet normal distribution or variance homogeneity, the non-parametric test was used.

III. Experimental Results

1. Detection of VEGF in Mouse-Eye Serum

Figure 4:
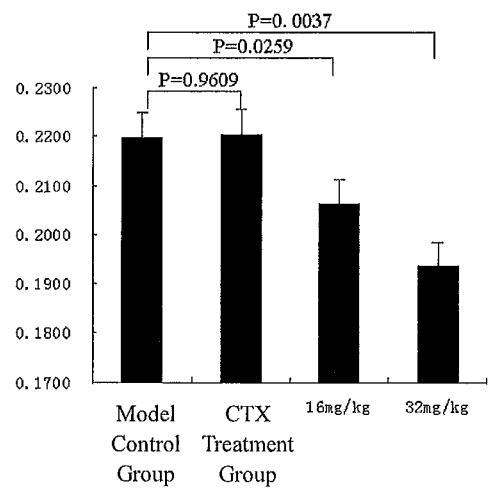
FIG. 4 shows the detecting results on mouse ocular blood VEGF.
Figure 5:
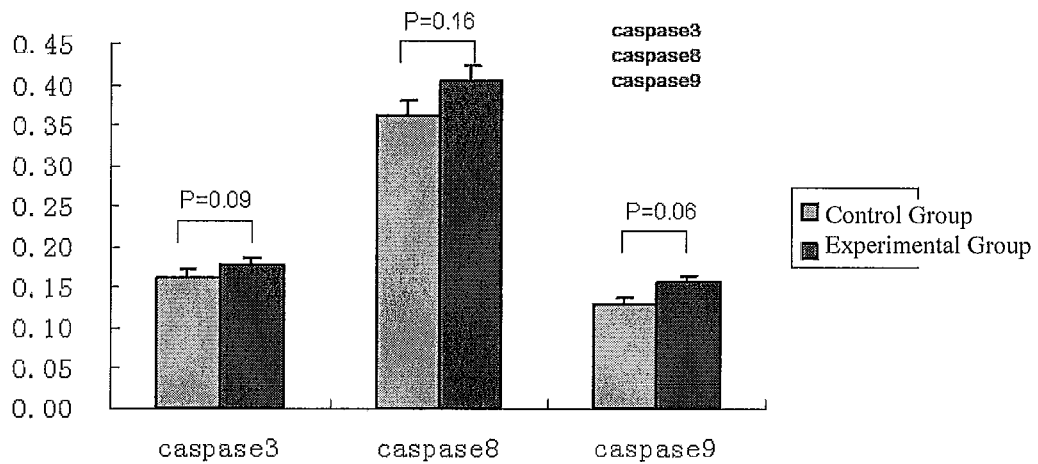
FIG. 5 shows the 24-hour detecting results of Caspase-3, 8, 9.

As shown in Table 4-3 and FIG. 4, the optical density value (OD value) of serum VEGF of mice in high dose group is 0.1937, when compared with the OD value 0.2200 of the negative control group, P=0.0037; for the low dose group, when compared with the negative control group, P=0.0259, both have statistical significance.

TABLE 4-3

Detection results of VEGF activity (x ± s)

| Groups | Negative control | Positive control | 16 mg/kg | 32 mg/kg |
|---|---|---|---|---|
| OD value | 0.2200 ± 0.0174 | 0.2205 ± 0.0238 | 0.2064 ± 0.0114□ | 0.1937 ± 0.0170□ |

Notes:
compared with the negative control, □P < 0.05, □P < 0.01.

2. Determination of Activity of Caspase 3, 8, 9

Figure 6:
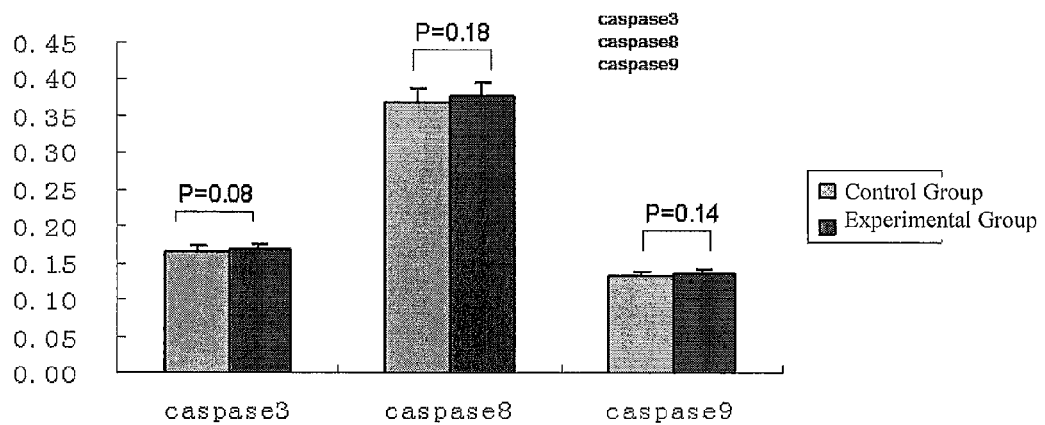
FIG. 6 shows the 48-hour detecting results of Caspase-3, 8, 9.

After CL168-6 working on HepG2 cells for 24 hours and 48 hours, the activity of Caspase 3, 8, 9 was determined and the relevant results were shown in Table 4-4 and FIG. 6.

TABLE 4-4

| | OD values of Caspase 3, 8, 9 | | | |
|---|---|---|---|---|
| | 24 h | | 48 h | |
| | 0 μg | 2.0 μg | 0 μg | 2.0 μg |
| Caspase3 | 0.163 | 0.190 | 0.165 | 0.185 |
| Caspase8 | 0.362 | 0.413 | 0.368 | 0.408 |
| Caspase9 | 0.130 | 0.156 | 0.132 | 0.146 |

Activities of the three Caspases were not significantly increased, and therefore have no statistical significance.

Figure 7:
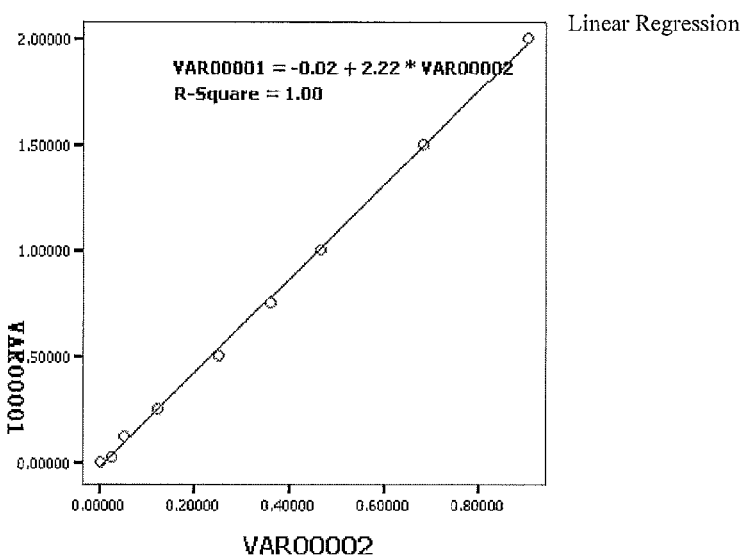
FIG. 7 illustrates a protein standard curve.

3. Protein Electrophoresis 3.1 Determination of Cell Extract Protein Concentrations (FIG. 7)

Protein standard curve was drawn according to the concentrations (x) and absorbencies (y) of the BSA standards. Linear equation Y=2.22x−0.02 was obtained by using the standard curve, wherein Y represents concentrations of the diluted samples, and x represents absorbencies. As shown in FIG. 3.3, that related coefficient r=1.00 means good correlation of the linear equation. The corresponding protein concentration (x) was calculated based on the determined absorbance value (y).

3.2 Expression of P53 Protein Level

Figure 8:
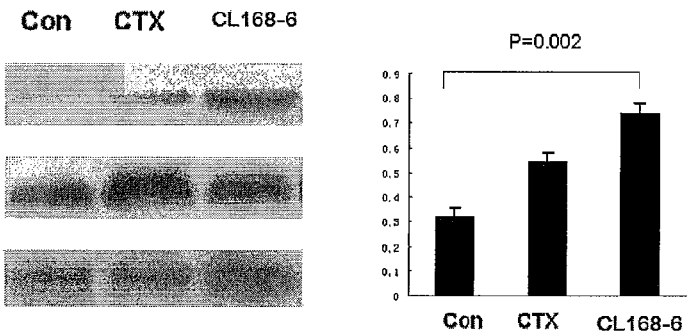
FIG. 8 shows the expression level of p53 (n=3).

During protein electrophoresis, the total protein amounts of samples on each well were consistent to one another. The three groups were a negative control group, a positive control group (CTX) and a CL168-6 experimental group. β-Actin was inner reference standard. For the experimental group, the relative expression level of P53 was 0.74±0.03; while for the negative control group, it was 0.32±0.05; there was significant difference between the two groups, P=0.002. (FIG. 8)

3.3 Expression of bcl-2 Level

Figure 9:
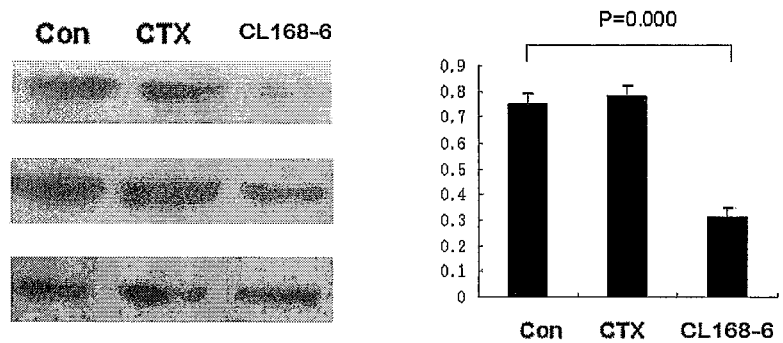
FIG. 9 shows the expression level of bcl-2 (n=3).

For the experimental group, the relative expression level of bcl-2 was 0.75±0.04; while for the negative control group, it was 0.31±0.01; P=0.000; both of the two groups had statistical significance. (FIG. 9)

3.4 Expression of VEGF Level

Figure 10:
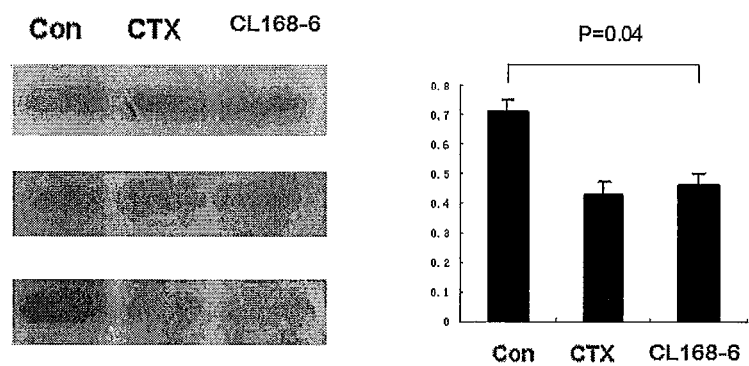
FIG. 10 shows the expression level of VEGF (n=3).

For the experimental group, the relative expression level of VEGF was 0.46±0.08; while for the negative control group, it was 0.71±0.05; there was significant difference between the two groups, P=0.04. (FIG. 10)

3.5 Expression of P21 Level

Figure 11:
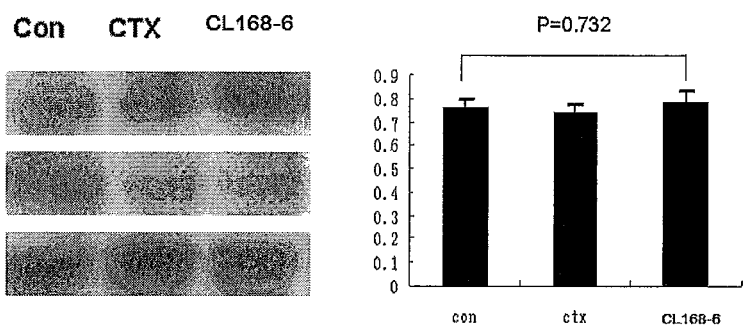
FIG. 11 shows the expression level of P21 (n=3).

For the experimental group, the relative expression level of P21 was 0.79±0.07; while for the negative control group, it was 0.76±0.06; there was no significant difference between the two groups, P=0.73. (FIG. 11)

IV. Conclusion

The present experimental study shows that CL168-6 can decrease the VEGF level in eye blood of a tumor-bearing mouse; at the same time, the level of VEGF protein expression in the tumor had a downward trend. CL168-6 can inhibit tumor proliferation by reducing the activity of VEFG.

Our experiment shows that CL168-6 had no significant effect on the activities of Caspase 3, 8, 9. It is supposed that CL168-6-induced apoptosis in HepG2 cells may not depend on the activation of these three enzymes.

In the present experiment, since expression levels of P21 protein of the control group and the treatment group had no statistical significance, it can be concluded preliminarily that the tumor-inhibitory effect of CL168-6 is not achieved by the signal transduction pathway of P53→P21.

It was found in the experiment that, the expression level of Bcl-2 protein of the treatment group was significantly lower than that of the negative control group. It can be concluded that CL168-6 can achieve the tumor-inhibitory effect by reducing the expression level of Bcl-2 protein. The specific mechanism is to be further explored.

P53 gene has two types. One is Wild type p53, i.e. wtp53, the other is Mutant type p53, i.e. mtp53. Wtp53 is a tumor suppressor gene, can be involved in cell cycle regulation, and plays an important role in the procedures of maintaining normal growth of cells and inhibiting tumor proliferation. Our experimental results show that the expression level of P53 protein of the treatment group is significantly higher than that of the negative control group. Then it can be concluded preliminarily that, CL168-6 can increase the expression level of wtp53 in the tumor-bearing mouse and inhibit the protein expressions of Bcl-2 and VEGF so as to achieve the anti-tumor effect.

Toxicity Example 1

I. Experiment Item: Intraperitoneal injection $LD_{50}$ for mouse (KORBER's method)

II. Experimental Materials

ICR mice [male/female=1/1, 18-22 g, Animal License No.: SCXK(Beijing)2007-0001];

CL168, white power (prepared by ourselves), diluted with salad oil, prepared before use.

III. Experimental Method

ICR mice (SPF grade), with a weight range of 18-22 g, provided by Vital River Laboratories (VRL) in Beijing, China, were used. There were 5 treatment groups in total, wherein 2000 mg/kg was the highest dose, and the others decreased to 0.8 times, i.e. 1600 mg/kg, 1280 mg/kg, 1024 mg/kg and 819.2 mg/kg. The mice were randomly divided into groups. Each group had 10 mice with half male and half female. Each mouse was introperitoneal injected (0.2 ml/10 g. Observed 3-7 days, a variety of animal responses and the amount of dead mice in each group were recorded. $LD_{50}$ and confidence limits were calculated by the modified Karber method(Korbor) according to the mortality rate of animals in each group.

IV. Experimental Result

In the 12 hours after administration, no death appeared. Death situation of mice in each group in 7 days were listed in the following table.

Table in the Example: Intraperitoneal injection $LD_{50}$ for CL168 mouse

| Group No. | Number of animals | Administration Dose (mg/kg) | Logarithmic dose (X) | Animal deaths | Mortality rate (P) | $P^2$ |
| --- | --- | --- | --- | --- | --- | --- |
| 1 | 10 | 819.2 | 2.91 | 0 | 0 | 0 |
| 2 | 10 | 1024 | 3.01 | 1 | 0.1 | 0.01 |
| 3 | 10 | 1280 | 3.11 | 3 | 0.3 | 0.09 |
| 4 | 10 | 1600 | 3.20 | 6 | 0.6 | 0.36 |
| 5 | 10 | 2000 | 3.30 | 8 | 0.8 | 0.64 |

V. Summary $LD_{50}$ calculated by the modified Karber method(Korbor) for CL168-6 was 1479.11 mg/kg; 95% confidence interval was 1304.19-1677.49 mg/kg.

Toxicity Example 2

I. Experiment Item: the anti-tumor therapeutic index of CL168

II. Experimental Materials: please see Resulting Example 2 and Toxicity Example 1.

III. Experimental Method: please see Resulting Example 2 and Toxicity Example 1.

IV. Experimental Result: please see Resulting Example 2 and Toxicity Example 1.

V. It can be found from Resulting Example 2 that, when using a high dose (30 mg/kg) of CL168, the inhibition rate to solid tumor S180 was 54.58%, the survival rate of H22 ascites cancer mice was 51.55%; when using a low dose (15 mg/kg) of CL168, the inhibition rate to solid tumor S180 was 44.33%, the survival rate of H22 ascites cancer mice was 37.11%; in combination with Toxicity Example 1, it can be seen that $LD_{50}$ of CL168 was 1479.11 mg/kg, and the therapeutic index (TI) thereof was about 49.3.

VI. Summary

The fact "the therapeutic index (TI) of CL168 was about 49.3" indicates that CL168 has high security and significant anti-tumor effect.

Formulation Example 1

10 g CL168-6 and suitable excipients for injection (including freeze-dried powder and sterile packing dry powder) were mixed and prepared into anti-tumor injections by injection (including freeze-dried powder and sterile packing dry powder) process.

Formulation Example 2

10 g CL168-6 and suitable excipients for tablet (including slow-release tablet, matrix tablet, coated tablet, dispersible tablet, etc.) were mixed and prepared into anti-tumor tablets by tablet (including slow-release tablet, matrix tablet, coated tablet, dispersible tablet, etc.) process.

Formulation Example 3

10 g CL168-6 and suitable excipients for capsule were mixed and prepared into anti-tumor capsules by capsule process.

Formulation Example 4

10 g CL168-6 and suitable excipients for emulsion (including microemulsion, nanoemulsion, etc.) were mixed and prepared into anti-tumor emulsions by emulsion (including microemulsion, nanoemulsion, etc.) process.

Formulation Example 5

10 g CL168-6 and suitable excipients for granule were mixed and prepared into anti-tumor granules by granule process.

Formulation Example 6

10 g CL168-6 and suitable excipients for controlled-release preparation were mixed and prepared into anti-tumor controlled-release preparations by controlled-release preparation process.

Formulation Example 7

10 g CL168-6 and suitable excipients for oral liquid were mixed and prepared into anti-tumor oral liquids by oral liquid process.

Formulation Example 8

10 g CL168-6 and suitable excipients for lipidosome were mixed and prepared into anti-tumor lipidosomes by lipidosome process.

The invention claimed is:

1. Compound CL168 represented by a structural formula I,

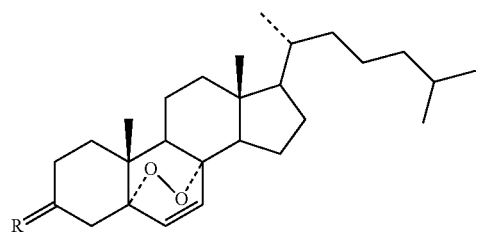

wherein R represents oxygen, sulfur, NH or $SO_2$.

2. A method of inhibiting proliferation of liver cancer and lung cancer cells in an individual comprising administering a therapeutically effective amount of a compound according to claim 1 to the individual.

3. A method of inhibiting angiogenesis in an individual comprising administering a therapeutically effective amount of a compound according to claim 1 to the individual.

4. The method of claim 2, wherein the compound of claim 1 decreases protein expression of Bcl-2 and vascular endothelial growth factor in the individual.

5. The method of claim 2, wherein the compound of claim 1 increases the gene expression of wtp53 in the individual.

6. The method of claim 2, wherein the compound of claim 1 inhibits the proliferation of hepatoma cells in the individual.

* * * * *